(12) United States Patent
Breen (10) Patent No.: US 7,793,659 B2
(45) Date of Patent: Sep. 14, 2010

(54) BYMIXER APPARATUS AND METHOD FOR FAST-RESPONSE, ADJUSTABLE MEASUREMENT OF MIXED GAS FRACTIONS IN VENTILATION CIRCUITS

(75) Inventor: Peter H. Breen, Irvine, CA (US)

(73) Assignee: The Regents of the University of California, Oakland, CA (US)

( * ) Notice: Subject to any disclaimer, the term of this patent is extended or adjusted under 35 U.S.C. 154(b) by 1131 days.

(21) Appl. No.: 10/530,602

(22) PCT Filed: Oct. 14, 2003

(86) PCT No.: PCT/US03/33072

§ 371 (c)(1),
(2), (4) Date: Nov. 14, 2005

(87) PCT Pub. No.: WO2004/032727

PCT Pub. Date: Apr. 22, 2004

(65) Prior Publication Data
US 2006/0201503 A1    Sep. 14, 2006

Related U.S. Application Data

(60) Provisional application No. 60/417,892, filed on Oct. 11, 2002.

(51) Int. Cl.
*A61M 16/00* (2006.01)
*A61M 15/00* (2006.01)

(52) U.S. Cl. .............................. 128/204.18; 128/200.24

(58) Field of Classification Search ............ 128/200.24, 128/203.12–204.18, 204.21
See application file for complete search history.

(56) References Cited

U.S. PATENT DOCUMENTS

| | | | | |
|---|---|---|---|---|
| 3,592,191 A | * | 7/1971 | Jackson | 128/203.28 |
| 4,206,754 A | * | 6/1980 | Cox et al. | 128/204.21 |
| 4,211,239 A | * | 7/1980 | Raemer et al. | 600/529 |
| 4,619,269 A | * | 10/1986 | Cutler et al. | 600/532 |
| 5,072,737 A | * | 12/1991 | Goulding | 600/531 |
| 5,239,994 A | * | 8/1993 | Atkins | 128/204.18 |
| 5,423,313 A | * | 6/1995 | Olsson et al. | 128/204.21 |
| 5,555,880 A | * | 9/1996 | Winter et al. | 128/204.21 |
| 5,605,148 A | * | 2/1997 | Jones | 128/205.11 |
| 5,701,883 A | | 12/1997 | Hete et al. | |
| 5,722,449 A | * | 3/1998 | Heinonen et al. | 137/101.19 |
| 5,752,506 A | | 5/1998 | Richardson | |
| 5,890,490 A | * | 4/1999 | Aylsworth et al. | 128/203.12 |
| 5,967,141 A | * | 10/1999 | Heinonen | 128/203.12 |
| 6,014,890 A | | 1/2000 | Breen | |
| 6,196,222 B1 | * | 3/2001 | Heinonen et al. | 128/204.23 |
| 6,279,574 B1 | | 8/2001 | Richardson et al. | |
| 6,298,848 B1 | * | 10/2001 | Skog | 128/204.18 |
| 6,408,848 B1 | * | 6/2002 | Feldman et al. | 128/205.14 |
| 6,571,796 B2 | * | 6/2003 | Banner et al. | 128/204.26 |
| 6,648,832 B2 | * | 11/2003 | Orr et al. | 600/532 |

\* cited by examiner

*Primary Examiner*—Justin R Yu
*Assistant Examiner*—Annette F Dixon
(74) *Attorney, Agent, or Firm*—Robert D. Buyan; Stout, Uxa, Buyan & Mullins (57) ABSTRACT

A bymixer device and method which provides fast-response, accurate measurements of mixed inspired and/or expired gas fractions in open or closed ventilation circuits and/or in circle circuits used in anesthesia and/or critical care. The bymixer device may include a main flow channel and a bypass flow channel. The bypass flow channel includes a flow-restrictor (e.g, an orifice) that partially blocks the flow of respiratory gas through the bypass flow channel, a mixing chamber positioned upstream of the flow restrictor and a sampling apparatus (e.g., a port for withdrawing samples of gas from said mixing chamber and/or sensor(s) positioned within the mixing chamber).

32 Claims, 7 Drawing Sheets

BYMIXER APPARATUS AND METHOD FOR FAST-RESPONSE, ADJUSTABLE MEASUREMENT OF MIXED GAS FRACTIONS IN VENTILATION CIRCUITS

RELATED APPLICATION

This patent application claims priority to U.S. Provisional Patent Application Ser. No. 60/417,982 entitled "Bymixer Apparatus for Fast-Response, Adjustable measurement of Mixed Expired Gas Fractions in the Anesthesia Circle Circuit and Related Method" filed on Oct. 11, 1002, the entirety of which is expressly incorporated herein by reference.

STATEMENT REGARDING FEDERALLY SPONSORED RESEARCH OR DEVELOPMENT

This invention was made with Government support under Grant R01 HL-42637 awarded by the National Institutes of Health. The Government has certain rights in this invention.

FIELD OF THE INVENTION

The present invention relates generally to biomedical devices and methods, and more particularly to devices and methods for anesthesia, critical care medicine, ventilation and monitoring of pulmonary function.

BACKGROUND OF THE INVENTION

Carbon dioxide ($CO_2$) is normally produced in the tissues of the human body where it becomes dissolved in the blood. The $CO_2$ is then transported in blood to the lung where it diffuses across alveolar membranes and is expelled from the lungs during exhalation.

The term "capnography" refers generally to the measurement of $CO_2$ in airway gas during the ventilation cycle. In patients who are undergoing anesthesia or mechanical ventilation, capnography is sometimes used to measure the partial pressure of $CO_2$ ($PCO_2$) at the airway opening during the ventilation cycle. During the inspiratory phase of the ventilation cycle (i.e., inhalation), a flow of inspired respiratory gas passes through the airway opening. Such inspired respiratory gas typically contains little or no $CO_2$. Thus, during the inspiratory phase, the capnograph obtains an inspiratory baseline $PCO_2$ measurement of zero. During the second phase of the ventilation cycle (expiratory upstroke), alveolar gas from the respiratory bronchioles and alveoli begins to pass out of the patient's airway and the capnogram measures a rapid increase in $CO_2$ as the expiratory phase of the ventilation cycle proceeds. The third phase of the ventilation cycle is known as the "alveolar plateau," during which a relatively constant $PCO_2$ is measured at the airway opening. The $PCO_2$ of the expired respiratory gas at the end of this third phase of the ventilation cycle ($PETCO_2$) is typically of particular interest as it represents the last alveolar gas sampled at the airway opening during expiration. Finally, the fourth phase of the ventilation cycle is the inspiratory downstroke, during which the next inspiratory phase begins.

While these direct capnographic measurements at the airway opening do provide the clinician with important diagnostic information, the usefulness of such information is limited due to the fact that direct capnographic measurements of this type merely measure the partial pressure of $CO_2$ without relating such measurement to the volume of respiratory gas that is passing through the airway opening as the measurement is taken. In view of this shortcoming of traditional capnography, it is now believed that a measurement of volume-normalized average alveolar $PCO_2$ and pulmonary carbon dioxide elimination ($\dot{V}_{CO_2}$) are more clinically useful than the traditionally used end-tidal $PCO_2$ ($PETCO_2$).

Additionally, anesthesiologists, pulmonologists and critical care physicians are now beginning to consider another measurable variable known as "pulmonary carbon dioxide elimination per breath ($\dot{V}_{CO_2,br}$)." $\dot{V}_{CO_2,br}$ is arrived at by multiplication and integration of the airway flow and $PCO_2$ of the respiratory gas over all four phases of the respiratory cycle.

Also, there is growing acceptance of a technique known as indirect calorimetry (e.g., the measurement and/or computation of $CO_2$ elimination and $O_2$ uptake) during anesthesia or mechanical ventilation for the rapid detection of various untoward states such as metabolic upset (e.g. onset of anaerobic metabolism) or pulmonary embolism.

The measurement of pulmonary carbon dioxide elimination ($\dot{V}_{CO_2}$), pulmonary oxygen uptake ($\dot{V}_{O_2}$) and other indirect calorimetric measurements are facilitated by sampling of mixed respiratory gas. Such sampling of mixed respiratory gas may be accomplished in several ways. One way is to attach a collection vessel such as a bag to the ventilation circuit to collect expired respiratory gas over a period of time. This collection technique is time consuming and of limited value because the collected mixture of respiratory gas is obtained from only one location in the ventilation circuit (e.g., from the expiratory flow conduit). Another technique for sampling mixed respiratory gas is through use of an in-line bymixer device. The bymixer devices of the prior art have been constructed to continually divert a portion of respiratory gas flowing through a conduit into a reservoir. Sanjo, Y., Ikeda, K., *A Small Bypass Mixing Chamber for Monitoring Metabolic Rate and Anesthetic Uptake*, J. Clin. Monit. 1987; 3: 235-243; Breen P. H., Serina E. R., *Bymixer Provides On-Line Calibration of Measurement of Volume Exhaled Per Breath*, Ann. Biomed. Eng. 1997; 25:164-171. However, such prior art bymixers were typically difficult to construct and thus somewhat expensive. Also, the gas collection reservoirs of such prior art bymixers were of constant volume and the gas diverting tubes were of constant dimensions and, thus, could not be rapidly adapted or adjusted to accommodate patients of varying size (e.g., small pediatric patients and large adult patients) or changes that may occur in a particular patient's ventilation parameters or clinical status. Finally, the gas collection reservoirs of the prior art bymixers were prone to collect condensed water vapor and respiratory debris and were difficult to clean.

Accordingly, there remains a need in the art for the development of a new bymixer device that is simple and economical to use and is adjustable or adaptable so as to be useable in patients of varying size (e.g., small pediatric patients and large adult patients) and to optimize the continuing measurements made during a given procedure as changes occur in the ventilation circuit and/or in a patient's ventilation parameters or clinical status.

SUMMARY OF THE INVENTION

The present invention provides a new bymixer device and method for obtaining fast-response, accurate measurements of mixed expired gas fractions in various types of ventilation circuits, including open (non-rebreathing) circuits, closed (rebreathing) circuits, circle (rebreathing with optional added fresh gas) circuits, etc. The bymixer is of a novel parallel design, which facilitates adjustable response, easy cleaning, and construction from standard airway circuit components.

This bymixer may serve as a platform or enabling technology to facilitate further use of indirect calorimetry during anesthesia and/or mechanical ventilation in critical care settings.

In accordance with the present invention, there is provided a bymixer device that is connectable to a respiratory gas flow conduit in a ventilation circuit (e.g., an open circuit, a closed circuit, a circle circuit, etc.) that is used for ventilating a human or veterinary patient. In general, the bymixer device of the present invention comprises a) a flow dividing manifold (e.g., a Y or T) for dividing the flow of respiratory gas into first and second flow streams, b) a main or direct flow channel that is connectable to the flow dividing manifold such that the first flow stream flows through the main flow channel, and c) a bypass flow channel that is connectable to the flow dividing manifold such that the second flow stream flows through the bypass flow channel. The bypass flow channel includes a flow-restrictor (e.g., an orifice or other flow-restricting structure) that partially blocks the flow of respiratory gas through the bypass flow channel, a mixing chamber positioned upstream of the flow restrictor and a sampling apparatus (e.g., a port for withdrawing samples of gas from said mixing chamber and/or sensor(s) positioned within the mixing chamber).

Further in accordance with the present invention, all or a portion of the bymixer device (e.g., the mixing chamber) may be automatically or manually adjustable or variable in size such that the volume of respiratory gas contained in the mixing chamber may be varied. In combination with, or separately from, such adjustability in the size of the mixing chamber, the degree of flow restriction caused by the flow restrictor may also be automatically or manually variable. The adjustability in mixing chamber size and/or degree of flow restriction allows the bymixer device to be adjusted or adapted in a manner that optimizes the rate of response in measurements made on mixed gas samples from the mixing chamber versus the homogeneity of the mixed gas samples obtained from the mixing chamber. Also, such adjustability of mixing chamber volume and/or flow rate through the mixing chamber allows the operator to adjust the bymixer to accommodate patients of varying size and/or to maintain optimal mixing of respiratory gas and monitoring of variables even when changes occur in the ventilation circuit or in a given patient's ventilation parameters and/or clinical status.

Still further in accordance with the present invention, one or more flow-disrupting surfaces and/or one or more mixing apparatus (e.g., mixing vanes, a rotating impeller, vibrating surface, moving member, etc.) may optionally be positioned in the mixing chamber to further enhance the mixing of respiratory gasses within the mixing chamber.

Further aspects of the present invention will become apparent to those of skill in the art upon reading and understanding the following detailed description and examples.

BRIEF DESCRIPTION OF THE DRAWINGS

FIGS. 4A and 4B are graphs depicting data generated by Bland-Altman analysis.

FIGS. 5A and 5B are graphs showing the effect of mixing chamber volume on bymixer $P_{CO_2}$ during continuous sampling from the bymixer port (200 ml/min) by the side-stream gas analyzer. Data were digitally acquired at 100 Hz. Airway opening flow was processed by moving average filter over 7 data points to remove signal noise. For clarity, every $20^{th}$ data point was plotted for bymixer $P_{CO_2}$. Relative to the flow signal, $P_{CO_2}$ was advanced in time by transport delay, the time to aspirate gas through the sampling line. Transport delay was measured previously in a bench set-up. Respiratory frequency was 12 breath/min and tidal volume was 600 ml. With the mixing chamber volume of 100 ml (upper panel), oscillations in bymixer $P_{CO_2}$ were about 1.3 mm Hg. The larger mixing chamber of 200 ml (lower panel) generated only tiny oscillations in bymixer $P_{CO_2}$ of about 0.2 mm Hg.

DETAILED DESCRIPTION

The following detailed description, and the accompanying drawings to which it refers, are provided for the purpose of describing and illustrating certain examples or specific embodiments of the invention only and not for the purpose of exhaustively describing all possible embodiments and examples of the invention. Thus, this detailed description does not in any way limit the scope of the inventions claimed in this patent application or in any patent(s) issuing from this or any related application.

Figure 1:
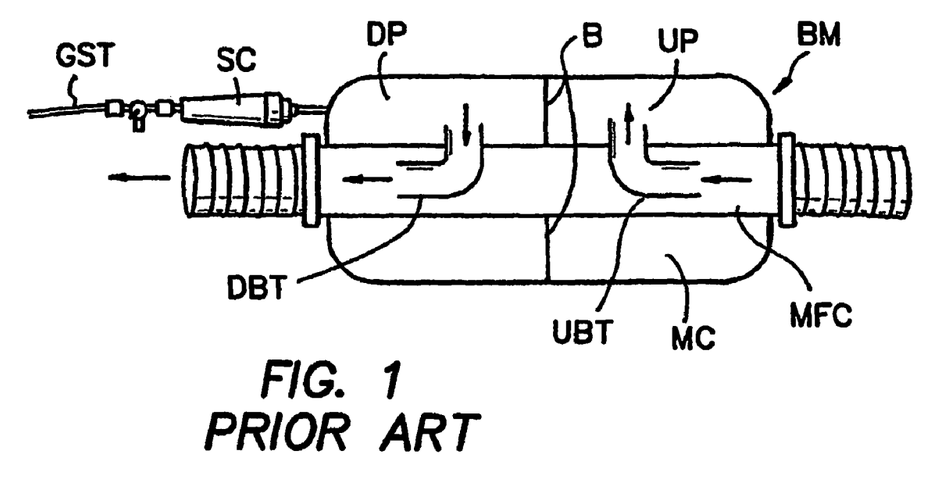
FIG. 1 is a schematic showing of a bymixer device of the prior art.

As shown in FIG. 1, a typical bymixer device of the prior art comprised a main flow conduit MFC that extends through a sealed mixing chamber MC. A right-angled upstream bypass tube UBT and a right-angled downstream bypass tube DBT extend through openings formed at longitudinally spaced-apart locations in the wall of the main flow conduit MFC, as shown. A porous baffle B divides the mixing chamber MC into an upstream portion UP and a downstream portion DP. A fraction of the respiratory gas flowing through the main flow conduit MFC would enter the upstream bypass tube UBT and would flow therethrough and into the upstream portion UP of the mixing chamber MC. Samples of mixed respiratory gas could be withdrawn from the downstream portion DP of the mixing chamber MC into the sample chamber SC where further mixing would occur and then through the gas sampling tube GST to the desired test apparatus where the desired analysis or measurement would be conducted. Mixed gas would also continually flow from the downstream portion DP of the mixing chamber MC, through the downstream bypass tube DBT and back into the main flow conduit MFC, thereby providing continual turnover of respiratory gas within the mixing chamber MC. This prior art bymixer has several limitations. For example, the size of the mixing chamber was fixed. Thus, the volume of gas within the mixing chamber could not be varied to optimize mixing of the respiratory gas or to respond to variations in patient size, physiology or clinical status. Similarly, the size and dimensions of the bypass tubes BP were fixed and could not be adjusted to vary the fraction of main flow into the mixing chamber MC. Also, the diameter of the upstream bypass tube was smaller than the diameter of the main flow conduit MFC and its position within the main flow conduit MFC was fixed. Thus, the sampling of gas was always obtained from the same region (e.g., the center) of the main flow conduit and in situations where flow though the main flow conduit is laminar, certain fractions of such laminar flow (e.g., that flowing though the periphery of the conduit) could flow past the upstream bypass tube UBT and would not be included in the sample shunted into the mixing chamber MC.

In clinical practice, there is substantial variation in the body size, respiratory physiology and clinical status of patients. Even during the course of a single procedure (e.g., a surgical procedure wherein the patient is connected to an anesthesia/ventilation circuit) there may be variations in the patient's respiratory physiology and/or clinical status. However, because the prior art bymixer (FIG. 1) had a mixing chamber MC of fixed size, it was not possible to adjust the size and/or volumetric capacity of the mixing chamber in response to such variations. Also, during manufacture, the positioning and securing of the upstream and downstream bypass tubes UBT, DBT was laborious and time consuming and the existence of these bypass tubes protruding into the lumen of the main flow conduit could, theoretically at least, result in trapping of condensed water vapor, microbes, mucoid matter or other contaminants.

Figure 2A:
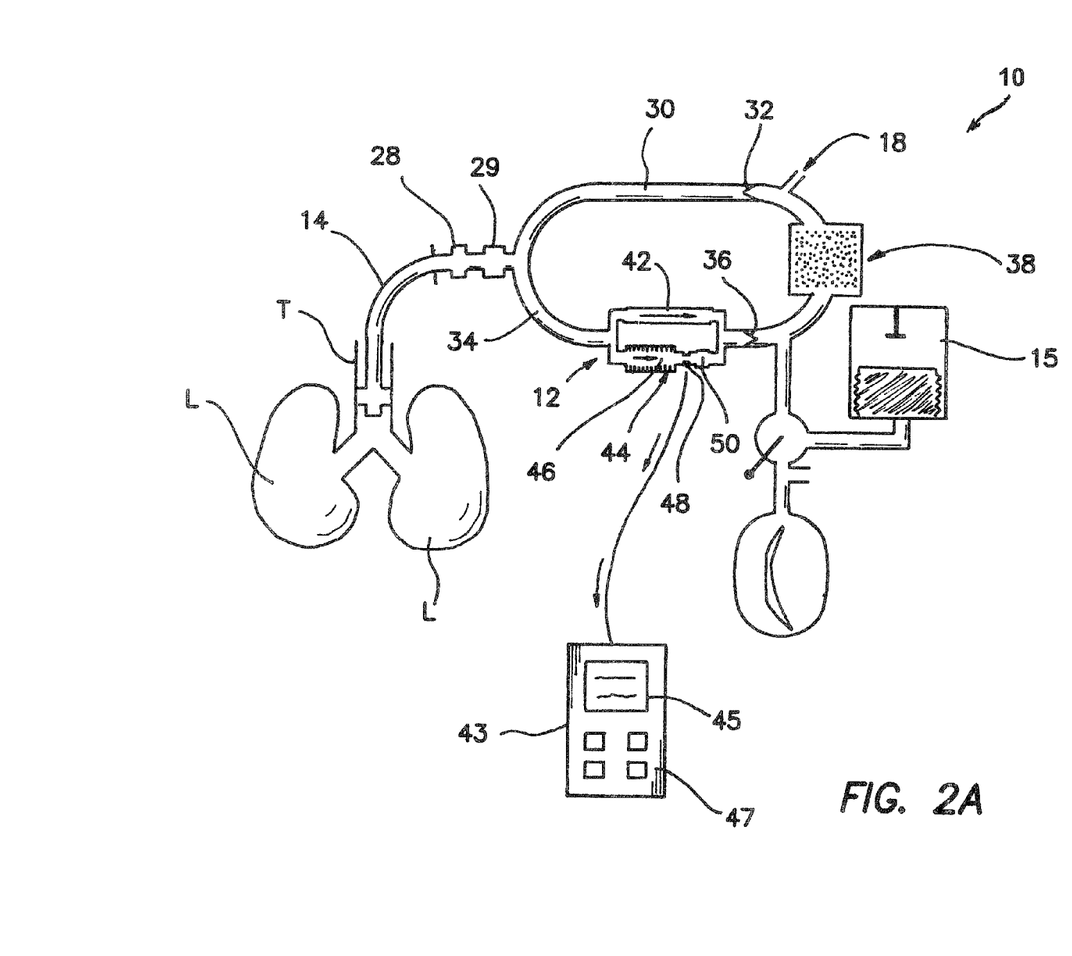
FIG. 2A is a schematic diagram of a circle-type ventilation circuit incorporating a bymixer device of the present invention.
Figure 2B:
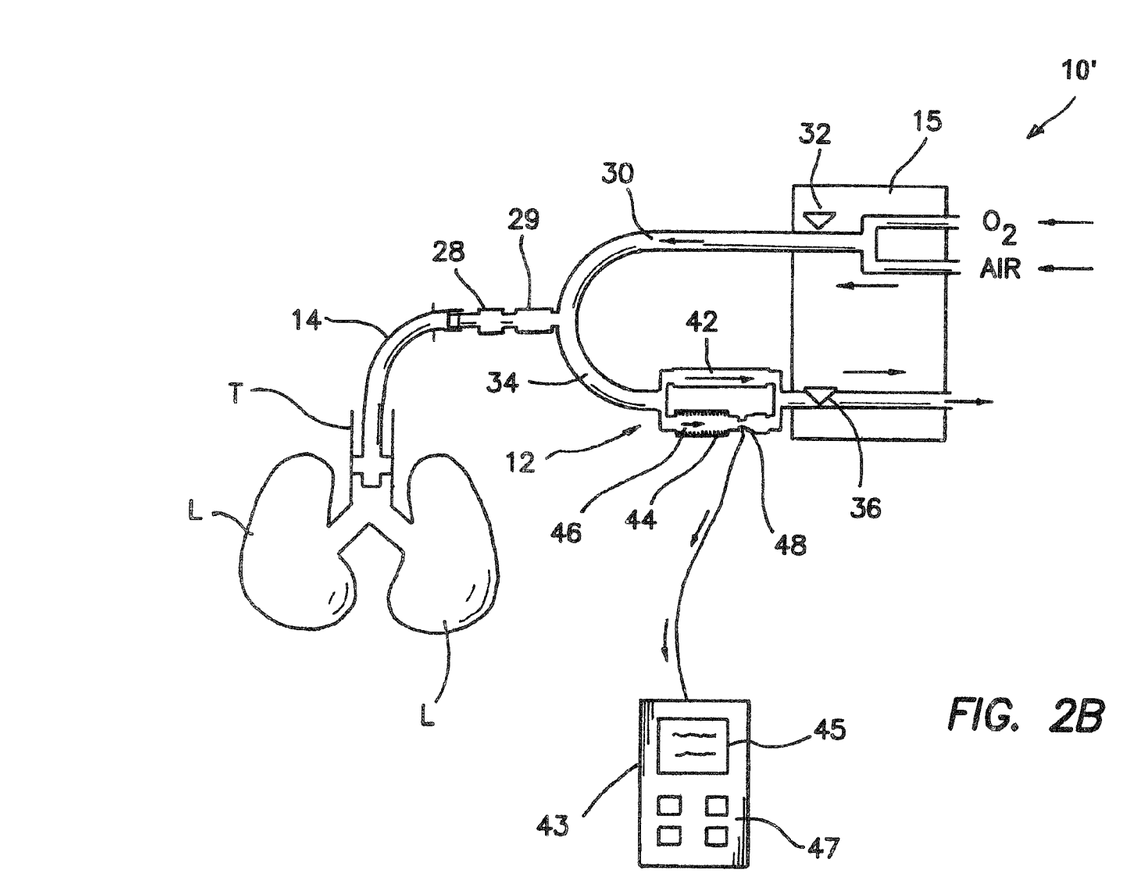
FIG. 2B is a schematic diagram of an open ventilation circuit incorporating a bymixer device of the present invention.
Figure 2C:
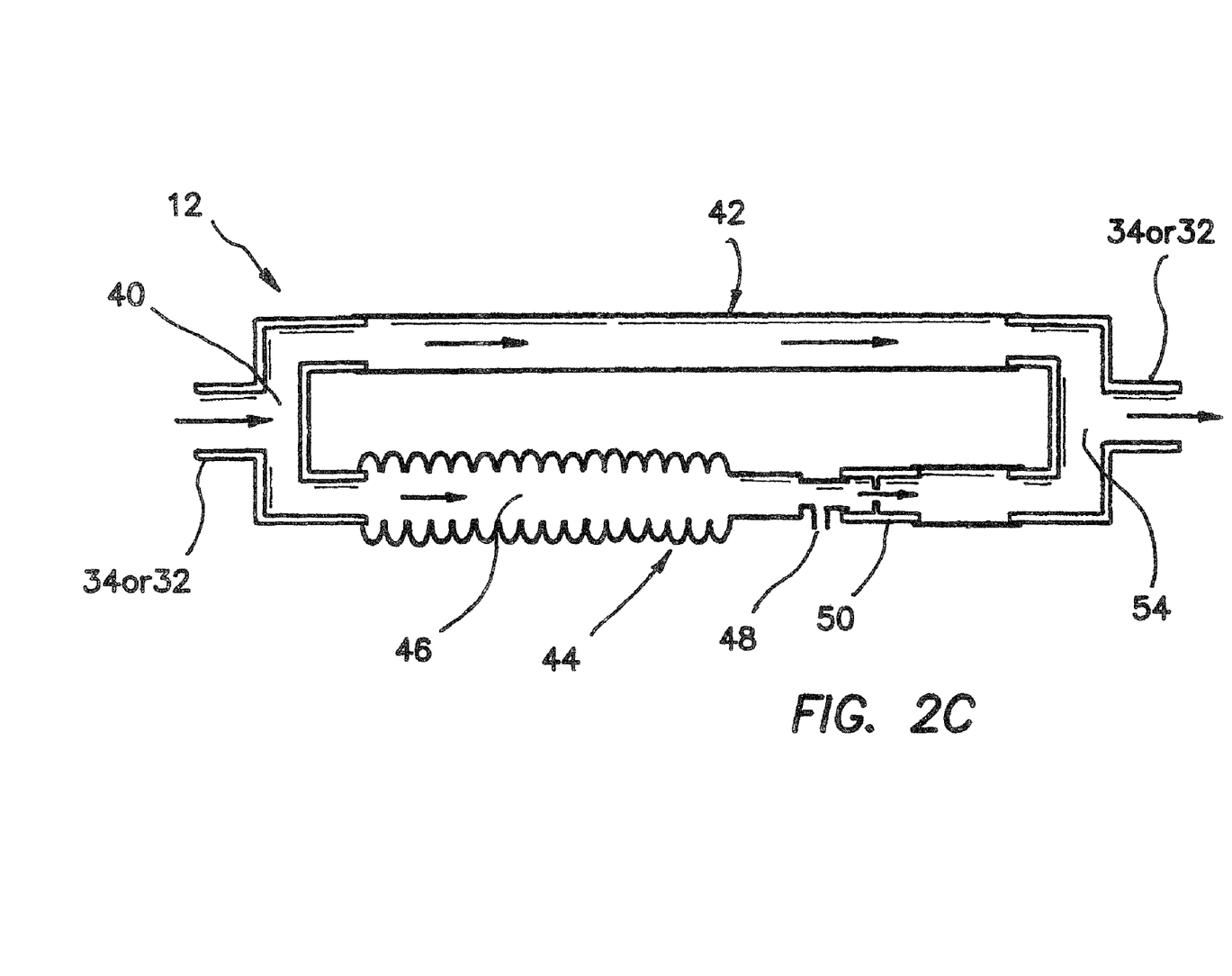
FIG. 2C is a longitudinal sectional view of a bymixer device of the present invention.

The bymixer device 12 of the present invention, as shown in FIGS. 2A, 2B and 2C, overcomes some or all of the shortcomings of the prior art bymixer. As explained herebelow, this new bymixer 12 is relatively simple and inexpensive to manufacture, relatively devoid of in-line obstructions and may optionally be adjustable in ways that allow the mixing chamber volume and/or the rate of flow through the mixing chamber to be modified or adjusted, thereby accommodating patients of varying body size, as well as differing or changing respiratory physiology and/or clinical status. Two types of ventilation circuits incorporating the bymixer 12 (a rebreathing circle circuit 10 and a non-rebreathing open circuit 10') are shown in FIGS. 2A and 2B, while details of the bymixer device 12 itself are shown in FIG. 2C.

Specifically, FIG. 2A shows an example of a circle ventilation circuit 10 which incorporates a bymixer 12 of the present invention. As shown, an airway device 14 such as an endotracheal tube, nasotracheal tube, tracheostomy tube, laryngeal mask airway or face mask is connected to the circle circuit 10 such that respiratory gas will flow into and out of the patient's lungs L. The circle circuit 10 comprises an inspiratory flow conduit 30 having a one-way inhalation valve 32 and an expiratory flow conduit 34 having a one-way exhalation valve 36, as shown, to alternately allow inspiratory inflow and expiratory outflow into and out of the patient's lungs L. During inspiration, inspiratory respiratory gas flows through inhalation valve 32, through inspiratory flow conduit 30, through the breathing device 14 and into the patient's lungs L. Thereafter, during expiration, respiratory gas is expelled from the patient's lungs L, though the airway device 14, though exhalation valve 36 and though the expiratory flow conduit 34. A pneumotachometer 29 and humidity/temperature sensor 28 are mounted near the airway device 14 to monitor respiratory rate, gas flow, humidity and temperature. The humidity/temperature sensor 28 may be any suitable type of humidity sensor, such as that described in U.S. Pat. No. 6,014,890 (Breen) entitled Fast Response Humidity and Temperature Sensor Device, the entirety of which is expressly incorporated herein by reference. In the example shown in FIG. 2A, the bymixer 12 of the present invention is attached to the expiratory flow conduit 34 such that expiratory respiratory gas flowing though the conduit 34 will enter a flow dividing manifold 40 (e.g., a Y or T) which channels a portion of that flow into a main flow channel 42 and a portion of that flow into a bypass channel 44.

As may be seen clearly in the enlarged sectional view of FIG. 2C, the bypass channel 44 comprises a mixing chamber 46, a flow restrictor 50 (e.g., an orifice) positioned downstream of the mixing chamber 46 and a sampling port 48 for withdrawing samples of mixed gas from the mixing chamber 46. It will be appreciated, however, that sampling of gas within the mixing chamber 46 may alternatively be accomplished without the need for withdrawal of gas through a sampling port by positioning one or more sensors (e.g., electrodes, optical sensors, chemical sensors, etc.) within the interior of the mixing chamber so that sample measurements may be made within the mixing chamber 46. Respiratory gas that has passed though the main flow channel 42 and bypass channel 46 then enters a flow combining manifold 54 (e.g., another Y or T) where it is recombined and continues through the downstream portion of the expiratory flow conduit 34.

In some embodiments of the invention, a monitoring device 43 may be connected to the sampling port 48 by a sampling tube 41 such that continuous or periodic samples of mixed gas may be withdrawn from the sample port 48 into the monitoring device 43. The monitoring device 43 may be operative to analyze, measure and/or otherwise determine any desired variables, such as volume-averaged expired $PCO_2$ ($PE_{CO_2}$), pulmonary carbon dioxide elimination ($\dot{V}_{CO_2}$), pulmonary oxygen uptake ($\dot{V}_{O_2}$), concentration or partial pressure of volatile gases (e.g., anesthetic gases), concentration or partial pressure of non-volatile gases, and/or other variables. In some instances, the monitoring device may incorporate a computer, microprocessor or other calculating apparatus and may be programmed or otherwise adapted to calculate one or more calculated values of interest based on one or more of the measured variables. In some instances, additional data such as patient body weight, barometric pressure, airway opening gas humidity and temperature, airway opening gas flow etc. may be input into the monitoring device 43, either by manual input (e.g., via a keyboard) or may be communicated by hard wired or wireless connection between the monitoring device 43 and one or more sensing apparatus operative to measure such values. These additional data (when obtained) may also be used in calculating some calculated values of interest. Examples of calculated values that may optionally be provided by the monitoring device include but are not limited to: pulmonary carbon dioxide elimination ($\dot{V}_{CO_2}$), pulmonary carbon dioxide elimination per breath ($V_{CO_2,br}$), pulmonary oxygen uptake ($\dot{V}_{O_2}$), pulmonary oxygen uptake per breath ($V_{O_2,br}$), minute ventilation ($\dot{V}_E$), tidal volume ($V_T$), Vital Capacity (VC), etc. The monitoring device 43 may include, or may be connected to, a display for displaying the measured variables and/or or computed values. For example, a waveform display 45 may provide a display of one or more waveforms such as flow, pressure, capnography, oxygen concentration, spirometry, etc. and/or one or more alphanumeric displays 47 (e.g., LED displays) may display numerical values and/or letters relating to variables or computed values such as such as those stated hereabove determined using the bymixer, as well as others such as peak inspiratory pressure, end tidal $CO_2$, expired $O_2$, inspired $O_2$, $CO_2$ elimination, $\dot{V}_{CO_2}$ and $O_2$ uptake, $\dot{V}_{O_2}$, tidal volume, minute volume, airway pressure, airway compliance, estimated energy required (EER), respiratory quotient (RQ), etc. In particular, the Respiratory Quotient (RQ) is a determined parameter calculated from the quotient of pulmonary carbon dioxide elimination ($\dot{V}_{CO_2}$) and pulmonary oxygen uptake ($\dot{V}_{O_2}$). The Respiratory Quotient is a very sensitive indicator of the metabolic state of the patient, particularly in its ability to detect the change from aerobic to anaerobic metabolism. The Respiratory Quotient depends only upon inspired and mixed expired gas fraction measurements for its calculation, and in particular, does not require any flow measurements. Thus, with a bymixer 12 on the expiratory flow conduit 34 (e.g., expired air limb of the ventilation circuit) and possibly, as necessary, another bymixer 12 on the inspiratory flow conduit 30 (e.g., the inspiratory limb of the ventilation circuit), the Respiratory Quotient can be measured and determined without the need for any flow measuring device.

One example of a monitoring device 43 that may be used is the Capnomac Ultima available commercially from Datex Medical Instruments, Instrumentarium Corp., Helsinki, Finland. Another example is the Datex-Ohmeda Division, Instrumentarium Corp. (Helsinki, Finland; Madison, Wis.) Airway Module, M-CAiOVX (gas composition/indirect calorimetry) and S/5 portable compact monitor, which can measure airway oxygen uptake and carbon dioxide elimination. The bymixer apparatus 12 can provide accurate, on-line and simultaneous measurements of $\dot{V}_{CO_2}$ and $\dot{V}_{O_2}$ to provide calibration values for the M-CAiOVX measurements. In at least some applications it may be of value to have a bymixer 12 of the present invention in a ventilation circuit in addition to another device for breath-by-breath calorimetric measurements at the patient's airway, such as the Datex-Ohmeda Airway Module, M-CAiOVX (gas composition/indirect calorimetry) and S/5 portable compact monitor. In this regard, the simultaneous side stream analysis/measurement of gas fractions at the airway opening, along with a measurement of flow at the airway opening (such as with a pneumotachometer) will allow the generation of breath-by-breath measurements of $VO_2$, $Vo_{2,BR}$ and $Vco_2$, and will allow the determination of $\dot{V}_{CO_2}$,br and $\dot{V}_{O_2}$,br via the online multiplication and integration on these gas fraction and flow values measured at the airway opening. The bymixer flow measurement of $\dot{V}_{O_2}$ during steady state can be used to calibrate these more unstable breath-by-breath measurements of indirect calorimetry. Then, during non-steady state conditions, were the bymixer flow measurement my not react fast enough to changes in patient pathophysiology, the breath-by-breath measurements maybe used to follow the patent's condition.

In some embodiments, the system may be fully or partially automated. For example, the system may include a programmable controller (e.g., a microprocessor or computer) that may receive input signal(s) from the monitoring device 48 and, in response to predetermined changes in measured variables or calculated values, may issue control signals to certain components of the system that are equipped to undergo changes in response to such automated control signals. For example, such automated control system may optimize the size of the mixing chamber 46 and/or the diameter of the flow restricting orifice 50. In some applications, it may suggest or facilitate changes in ventilator settings, such as $FiO_2$, respiratory rate, tidal volume, and positive end expiratory pressure (PEEP), to remedy undesirable changes or trends in measured variables or computed values.

Also, in some embodiments, the monitoring device 43 may also include one or more auditory or visual alarms that will be triggered when certain measured variables and/or computed values move outside of preset limits.

In the circle ventilation circuit 10 shown in FIG. 2A, the portion of the expiratory flow conduit downstream of the bymixer 12 flows into a $CO_2$ absorber 38 (e.g., SODA-SORB® 4-8 IND N MED, Daerx® Container Products, Cambridge, Mass. or ThermHOAbsorb™, Raincoat Industries, Inc., Louisville, Ky.) which removes $CO_2$ After exiting the $CO_2$ absorber 38, the expiratory flow (less $CO_2$ absorbed by the absorber 38) may be mixed with fresh gas (e.g., air and/or oxygen and/or nitrogen and/or anesthetic gas(es)) entering through fresh gas inlet 18, and flows through the inspiratory flow conduit 30 and back into the patient's lungs L as described above. This circle (rebreathing) ventilation circuit 10 may be used in various settings including during anesthesia where it is desired to recycle volatile or gaseous anesthetics and in certain other types of mechanical ventilation (including anesthesia) where it is desirable to prevent loss of the temperature and humidity of the expired respiratory gas and/or where it is undesirable to allow the expired respiratory gas to escape into the surrounding room air.

The open ventilation circuit 10' shown schematically in FIG. 2B includes many of the same components as the circle circuit 10 of FIG. 2A. However, in this open circuit 10', the expired respiratory gas is allowed to vent out of the circuit 10', downstream of the bymixer and only fresh respiratory gas enters the inspiratory flow conduit 30. This open (non-rebreathing) circuit 10' is typically used in mechanical ventilation of non-anesthetized critical care patients or during surgical procedures in which volatile or gaseous anesthetics are not used. Although FIGS. 2A and 2B show ventilation circuits 10, 10' in which the bymixer 12 is located on the expiratory flow conduit 34, it will be appreciated that the bymixer 12 may also be located on the inspiratory flow conduit 30 to obtain time-averaged or mixed samples of inspiratory respiratory gases.

Optionally, in some embodiments of the invention, the mixing chamber 46 is of variable size. This may be accomplished by constructing the mixing chamber of common corrugated tubing or other expandable or telescoping tubing such that the size and/or internal volume of the mixing chamber 46 may be varied. The advantages and clinical utility of this aspect of the invention are described more fully herebelow where reference is made to certain experimental data showing the utility of this feature as shown in FIGS. 3A-4B.

Optionally, in some embodiments of the invention, the flow restricting orifice 50 may be of variable size or diameter to permit the operator to easily adjust the flow rate of gas through the mixing chamber to optimize mixing.

Validation and Testing of Bymixer

Theoretical Background

Measurement of mixed expired gas concentrations is an essential component of the methodology to measure $CO_2$ elimination ($\dot{V}_{CO_2}$) and pulmonary oxygen uptake ($\dot{V}_{O_2}$) at the airway opening (1). In the normal condition where $CO_2$ is absent from inspired gas, $\dot{V}_{CO_2}$ is given by $$\dot{V}_{CO_2} = \dot{V}_E \cdot F\overline{E}_{CO_2} \quad \text{(Eq. 1)}$$

where $\dot{V}_E$ is the expired ventilation and $F\overline{E}_{CO_2}$ is the mixed expired $CO_2$ fraction.

On the other hand, $\dot{V}_{O_2}$ is the difference between inspired and expired $O_2$ volumes, as given by $$\dot{V}_{O_2} = \dot{V}_I \cdot F_{I_{O_2}} - \dot{V}_E \cdot F_{E_{O_2}} \quad \text{(Eq. 2)}$$

where I denotes inspiration. Because expired volume is increased by increased temperature (T) and added water vapor (increased humidity), volumes must be corrected to standard temperature and pressure, dry (STPD) conditions or the error in $\dot{V}_{O_2}$ can approach 50% as $F_{I_{O_2}}$ increases to unity. Because accurate differences between $\dot{V}_I$ and $\dot{V}_E$ are difficult to measure, the Haldane transformation is usually used, invoking conservation of the inert gas, nitrogen ($\dot{V}_I \cdot F_{I_{N_2}} = \dot{V}_E \cdot F_{E_{N_2}}$). By substitution into Eq. 2, $\dot{V}_{O_2}$ can be expressed as a function of only $\dot{V}_E$, where:

$$\dot{V}_{O_2} = \dot{V}_E \cdot (F_{I_{O_2}} \cdot F_{E_{N_2}} / F_{I_{N_2}} - F_{E_{O_2}}). \quad \text{(Eq. 3)}$$

Regardless of whether T and humidity differences between inspiration and expiration are managed by the Haldane transformation (Eq. 3) or by separate measurements of airway T and relative humidity (RH) (Eq. 2), the determination of $\dot{V}_{CO_2}$ and $\dot{V}_{O_2}$ requires measurements of mixed expired and inspired gas fractions. The classic method to obtain mixed expired gas fractions is to collect exhaled gas over a number of breaths in a collection chamber connected to the expiratory outlet of the ventilator. However, expired gas collection cannot be conducted in the anesthesia semi-open or closed anesthesia circle ventilating circuit because expired gas passes through a $CO_2$ absorber to become the next inspiration. Instead, to measure mixed expired gas fractions in the circle circuit, Applicant and other workers have used an inline bypass mixing chamber (e.g., a bymixer as shown in FIG. 1). The term "bymixer" is named for the by-pass of a constant fraction of total flow through a mix-ing chamber. However, the response time of that bymixer is long and fixed, the mixing chamber is difficult to fabricate, clean and sterilize, and the device is bulky.

To solve these problems, the bymixer 12 of the present invention may be constructed from common anesthesia circuit components (FIG. 2C). Instead of diverting gas flow into a separate, large mixing chamber, the new clinical bymixer incorporates a novel parallel tubing design. A constant fraction of total $\dot{V}$ is diverted through the mixing chamber 46 (e.g., corrugated collapsible/expandable pediatric anesthesia circuit tubing), whose volume can be adjusted (e.g., by collapsing or expanding the corrugated tubing). The resistor 50 controls the fraction of bypass $\dot{V}$ to total flow. As gas passes through the mixing chamber 46, it mixes longitudinally in the tubing. Flow-averaged mixed gas is sampled at the sampling port 48 for analysis by a side-stream sampling monitor 43.

In this study, the following questions were tested and answered: Is a constant fraction of main gas flow diverted through the mixing chamber (mandatory for mixed bypass gas samples to accurately represent total gas flow)? Does the longitudinal design of the tubular mixing chamber provide adequate mixing (no significant breath-to-breath variation of mixed gas fractions)? What is the fastest but still accurate response of the new clinical bymixer when the mixing chamber volume is decreased (shortest length of mixing tubing)? Does continuous side-stream sampling flow rate affect the measurement of mixed gas fraction?

In order to test the performance of the new bymixer 12 during cyclical changes in gas fractions under actual expiratory flow conditions, the bymixer 12 was interposed in the expiratory flow conduit 34 of a ventilation circuit that was attached to a $CO_2$-producing metabolic lung simulator as described in U.S. Provisional Patent Application Ser. No. 60/417,982, which is expressly incorporated herein by reference and in Rosenbaum, A, and Breen, P. H., *Novel, Adjustable, Fast Response Bymixer Measures Mixed Expired Gas Concentrations In Circle Circuit*, Anesth Analg; 97: pp. (2003). Measurement of bymixer mixed expired $P_{CO_2}$ was compared to the value in a gas collection from the exhaust port of the open circuit ventilator. The use of the metabolic lung simulator was mandatory for the execution of this study, in order to provide a wide and controlled range of tidal volume, respiratory frequency (f), and mixed expired $P_{CO_2}$.

Methods

Design and Construction of the New Clinical Bymixer).

The bymixer 12 divides incoming total gas flow into two parallel channels, a main flow channel 42 and a bypass flow channel 44. In the bymixer 12 used in this experiment, the main flow channel 42 was constructed of a 24 cm length of standard ¾ inch PVC pipe (22 mm ID). The mixing chamber 46 was a length of expandable/collapsible pediatric anesthesia circuit tubing (15 mm ID, Expandoflex, Cleveland Tubing Inc., Cleveland, Tenn.). This adjustable tubing was connected, in series, to the sampling port 48 which was constructed from a sampling port adapter available commercially from Datex-Engstrom Division, Instrumentarium Corp., Helsinki, Finland, a flow resistor 50, and a 12 cm length of standard ¾ inch PVC tubing. The flow resistor 50 was constructed by drilling a 4 mm diameter hole in a plastic cap (NAS-820-10, Niagra Plastics, Erie, Pa.), placed inside a connector (Multi Adapter, Hudson RCI, Temecula, Calif.; 15 mm ID, 22 mm OD). In this study, the adjustable tubing lengths were 50, 65.5, and 121 cm, which generated mixing chamber volumes (measured up to the sampling port) of 100, 150, and 200 ml, respectively. The volume of the bypass channel 44 from the sampling port 48 to the downstream "Y" connector 54 was 53 ml. The main flow channel 42 and bypass flow channel 44 were connected at each end by identical "Y" connectors 40, 54 (supplied with standard anesthesia circle circuits). Volumes of channel components were determined by water displacement.

Determination of Time Constant (Bymixer Response).

The anesthesia monitor (Capnomac Ultima, Datex Medical Instruments, Instrumentarium Corp., Helsinki, Finland) sampling line was connected to the bymixer sampling port (200 ml/min) and the pneumotachometer adapter was attached to the inlet of the bymixer. $F_{O_2}$ (paramagnetic) and bymixer total flow were continuously captured (100 Hz) by analog-to-digital (A/D) acquisition PC card (DAQcard 700, National instruments, Austin, Tex.) installed in a notebook computer (Inspiron 3800, Dell Computer Corp., Austin, Tex.). The digital data acquisition system was driven by a custom program (Delphi Pascal, Borland International, Scotts Valley, Calif.) written by our computer support specialist (David Chien) and one author (PHB). The bymixer was flushed with air to provide a baseline $F_{O_2}$ of 21%. At time zero, oxygen flow of either 4, 8, or 12 L/min was abruptly connected to the bymixer input. The time constant ($\tau$) was the time interval, from time zero, until $F_{O_2}$ increased to 63% of its maximal value (8). The time constant was corrected for the $F_{O_2}$ transport delay (2.95 sec) down the side-stream sampling system (9).

The bymixer response was also tested in the exhalation limb during mechanical ventilation of the $CO_2$-producing metabolic lung simulator. Steady state ventilation was established at minute ventilation of 4, 8, or 12 L/min (respiratory frequency, f, was 10/min and inspiration-to-expiration time ratio, I:E, was 1:2). The bymixer 12 (100 ml mixing chamber)

was separately flushed with air. During the inspiratory phase, the bymixer 12 was abruptly interposed in the expiratory flow conduit 34 of the ventilation circuit (time zero). Because bymixer data during ventilation was periodic and available only during expiration, Applicant used the time for bymixer $P_{CO_2}$ (infra-red analysis) to reach 95% of its maximum value. This time for 95% response was corrected for the $P_{CO_2}$ transport delay (1.76 sec) down the side-stream sampling system.

Validation of the Accuracy of the New Clinical Bymixer.

To test the bymixer 12, Applicant used a modification of the metabolic lung simulator bench setup. The commercial lung simulator (Dual Adult TTL, Model 1600, Michigan Instruments, Inc., Grand Rapids, Mich.) generated a physiologic ventilation waveform by combining airway resistance elements to a bellows (residual volume=920 ml), whose compliance can be adjusted by springs. The mechanical lung was connected by a circular circuit to a metabolic chamber (airtight 18.6 L pail). Carbon dioxide was continuously infused (200 ml/min) by calibrated rotameter into the metabolic chamber. A fan and a baffle system inside the chamber ensured a homogeneous gas mixture. An occlusion roller pump (15 mm ID tubing; Precision Blood Pump, COBE Perfusion system, Lakewood, Colo.) generated constant gas flow (5 L/min) between the metabolic chamber and the mechanical lung. The mechanical lung was ventilated with 30% oxygen (Servo Ventilator 900C, Siemens, Sweden). The bymixer 12 was interpolated in the expiratory limb of the open circuit (no rebreathing).

For each length of mixing chamber expandable tubing, the bymixer 12 was tested during different ventilatory patterns, encompassing combinations of tidal volume (300-1200 ml) and respiratory f (6-20 breath/min). I:E ratio was 1:2. Gas was continuously sampled from the bymixer by the side-steam capnometer (bymixer $P_{E_{CO_2}}$). Before measurements began at each ventilator setting, steady state was confirmed by stable values of $P_{ET_{CO_2}}$ and bymixer $P_{E_{CO_2}}$. A measurement sequence consisted of continuous digital acquisition of bymixer $P_{E_{CO_2}}$ and simultaneous collection of expired gas in a 15 L gas-impermeable collection bag (Hans Rudolph, Kansas City, Mo.) connected to the ventilator exhaust port. Measurements were conducted for 3 min (higher minute ventilation) to 5 min (lower minute ventilation). After the measurement sequence, the expired gas collection was mixed by shaking and agitating small balls inside the bag. Gas collection $P_{E_{CO_2}}$ was measured by attaching the side-stream sampling line to a stop-cock on the collection bag. Prior to each measurement sequence, the collection bag was emptied by vacuum to prevent gas dilution error. After attaining steady state and just before gas collection began, the dead space of the bag was flushed with exhaled gas from the ventilator exhaust port. Time-averaged bymixer $P_{E_{CO_2}}$ was compared to the value measured in the simultaneous expired gas collection.

Effect of Tidal Volume and Respiratory Frequency on Oscillations of Bymixer $P_{E_{CO_2}}$.

Using the above Validation experimental setup and measurement sequences in the bymixer (150 ml mixing chamber volume), Applicant conducted two additional protocols which measured oscillations of bymixer $F_{E_{CO_2}}$. First, respiratory frequency was held constant (10 br/min) and tidal volume was varied from 300 to 1200 ml. Second, tidal volume was held constant (900 ml) and respiratory frequency was varied from 6 to 20 br/min.

Effect of Intermittent (Instead of Continuous) Sampling From the Bymixer Port.

Applicant conducted an additional validation protocol using the bymixer 12 with its mixing chamber 46 volume set at 150 ml.). Gas was intermittently sampled from the bymixer sampling port 48, by manipulation of a 3-way stopcock, for short periods (about 3 sec). Several intermittent samples from the bymixer 12 were averaged for comparison with the expired gas collection (3-5 min), at each ventilator setting of tidal volume and frequency.

Data Analysis.

Bymixer bypass flow ($\dot{V}_{BYPASS}$) was calculated by $$\dot{V}_{BYPASS} = V_{BYPASS}/\tau, \qquad \text{Eq. 4}$$

where, $V_{BYPASS}$ was the volume of the mixing chamber (measured up to the sampling port), and $\tau$ was the measured time constant of the bymixer (4,8). Then, $$\text{Bymixer bypass ratio} = \dot{V}_{BYPASS}/\dot{V}_{TOTAL}, \qquad \text{Eq. 5}$$

where $\dot{V}_{TOTAL}$ was the total gas flow entering the bymixer.

In the validation of average bymixer $P_{CO_2}$ versus the value measured in the expired gas collection (metabolic lung simulator), $$P_{E_{CO_2}}^{bymixer} = \int_{t_0}^{t_{end}} P_{CO_2}(t) \cdot dt \Bigg/ (t_{end} - t_0), \qquad \text{Eq. 6}$$

where dt is the digital sampling interval (1/100 Hz) and $t_0$ and $t_{end}$ were the beginning and end sampling times (sec) of bymixer $P_{O_2}$.

Bymixer $P_{E_{CO_2}}$ were compared to expired gas collection $P_{E_{CO_2}}$ by least squares linear regression (slope, Y-intercept, and coefficient of determination, $R^2$) and by the limits of agreement technique described by Bland and Altman. Differences between groups were sought by t-test or by analysis of variance (ANOVA). Computer programs were used for data analysis (Excel spreadsheet, Microsoft Corp., Redmond, Wash.), statistical testing (SigmaStat, SPSS, Chicago, Ill.), and graphical presentation (SigmaPlot 8.0, SPSS).

Results

Figure 3A:
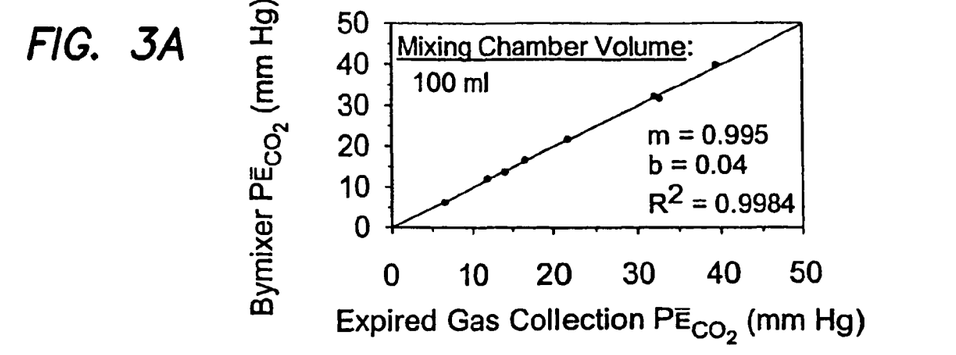
FIGS. 3A, 3B and 3C are graphs showing the correlation of bymixer mixed expired $P_{CO_2}$ ($PE_{CO_2}$) versus $PE_{CO_2}$ measured in a mixed collection of expired gas, for mixing chamber volumes of 100, 150, and 200 ml. Each plotted point represents a steady state ventilation sequence of a $CO_2$-producing lung simulator, over a range of tidal volume (300-1200 ml) and respiratory frequency (6-20 breath/min); m, slope; b, Y-intercept; and $R^2$, coefficient of determination (linear regression).
Figure 3B:
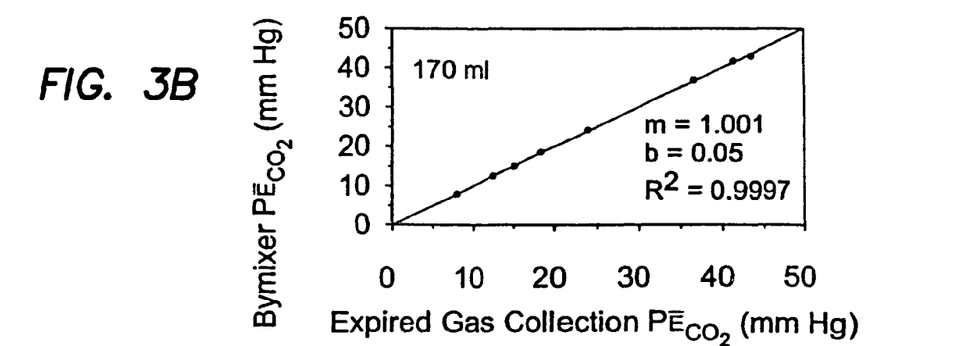
Figure 3C:
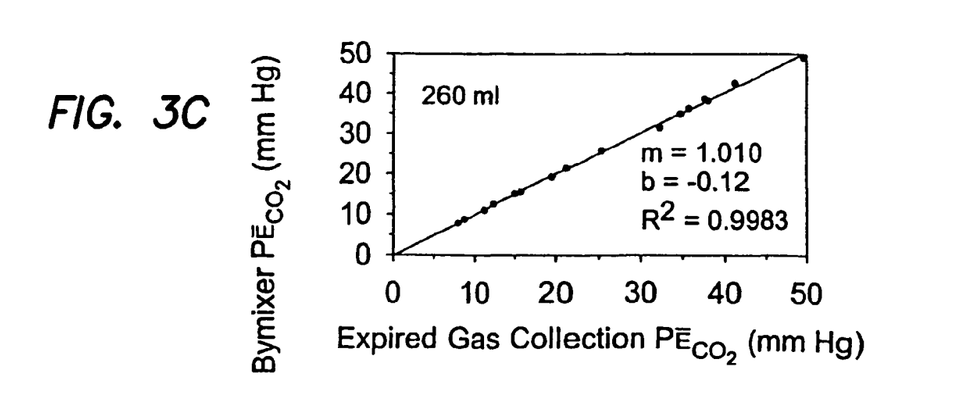

FIGS. 3A-C display the excellent linear regression correlation between bymixer $P_{E_{CO_2}}$ and the value measured in the expired gas collection over a wide range of $P_{E_{CO_2}}$ (6-50 mm Hg), for the bymixer with mixing chamber volumes set to 100, 150, and 200 ml. There was no significant difference in bymixer $P_{E_{CO_2}}$ accuracy among the mixing chamber volumes (ANOVA analysis of the $P_{E_{CO_2}}$ differences between the bymixer and expired gas collection measurements). For the bymixer set to mixing chamber volume of 150 ml, there was no significant difference in $P_{E_{CO_2}}$ accuracy between continuous and intermittent sampling from the bymixer port.

Figure 4A:
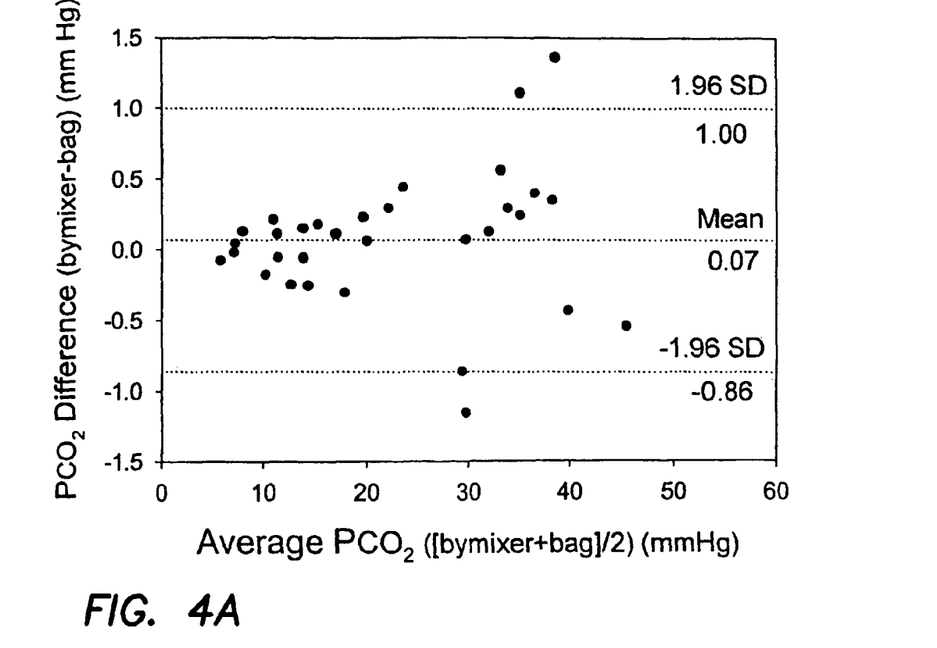
FIG. 4A shows the difference between the bymixer $P_{CO_2}$ and the value measured in the mixed collection of expired gas (exhaust gas collection bag) plotted against the average of the two values.
Figure 4B:
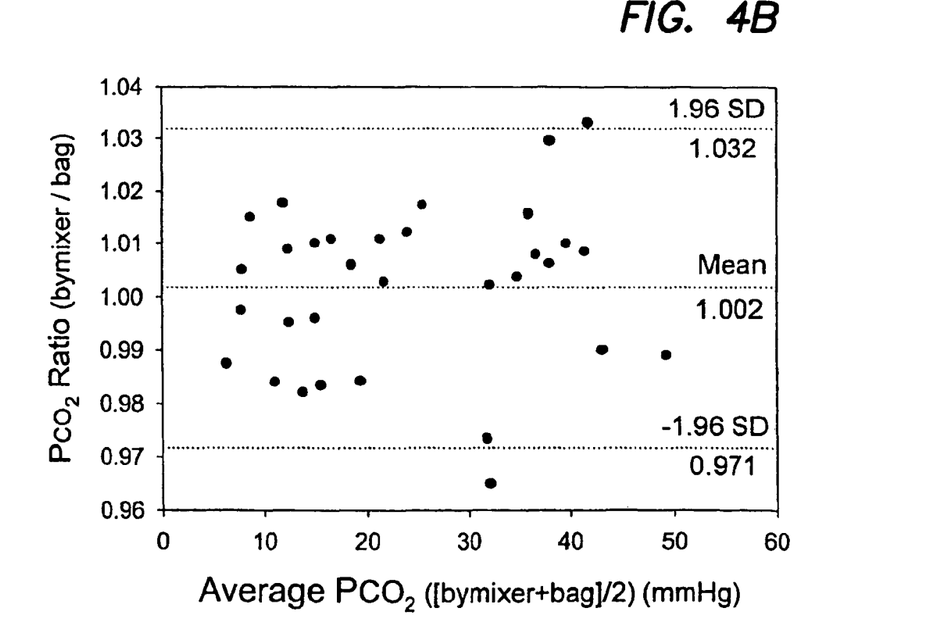
FIG. 4B shows the ratio of the bymixer $P_{CO_2}$-to-gas collection $P_{CO_2}$ plotted against the average of the two values. (Dotted lines denote the mean±1.96 standard deviations (SD), which encompass 95% of the measurement sequences. Each plotted point represents a steady state ventilation sequence of a $CO_2$-producing lung simulator, over a range of tidal volume (300-1200 ml) and respiratory frequency (6-20 breath/min). Measurements for mixing chamber volumes of 100, 150, and 200 ml are combined.)

The Bland-Altman analysis derived the Limits of Agreement (LOA) as 0.07±0.93 mm Hg (FIG. 4A). Measurements for mixing chamber volumes of 100, 150, and 200 ml were combined. Inspection of the graph revealed that the $P_{CO_2}$ difference, between the bymixer measurement and the simultaneous value measured in the expired gas collection, increased as the measurement increased along the x-axis. To correct for this effect, FIG. 4B plotted the $P_{CO_2}$ ratio (bymixer/bag) versus the average of the two values. The calculation of LOA (1.00±0.03) demonstrated that 95% of the bymixer $P_{CO_2}$ measurements were within 3% of the expired gas collection value.

Figure 5A:
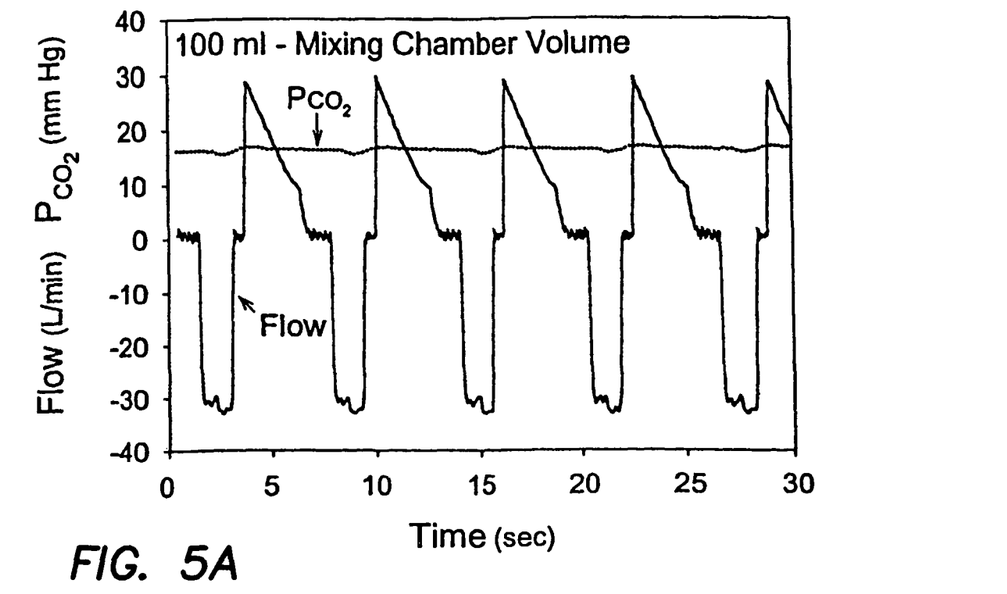
Figure 5B:
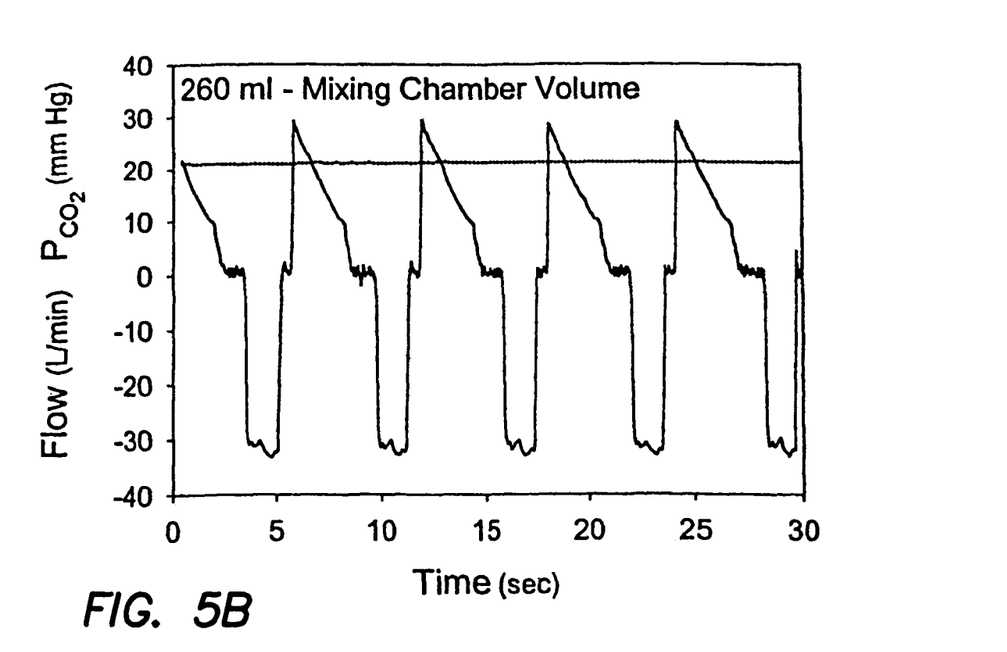

FIGS. 5A and 5B displays the breath-by-breath oscillations in $P_{CO_2}$ measured during continuous aspiration from the bymixer into the side-stream sampling gas analyzer. Oscillations in $P_{CO_2}$ were larger with the smaller bymixer mixing chamber volume. Table 1, below, displays that the average $P_{CO_2}$ oscillations increased from 0.1 to 0.7 mm Hg as bymixer mixing chamber volume decreased from 200 to 100 ml. The plot of $P_{CO_2}$ oscillation (mm Hg) versus $V_T$ (ml) (constant f) generated a significant direct relationship (slope=0.0016; Y-intercept=–0.69; $R^2$=0.92). The plot of $P_{CO_2}$ oscillation (mm Hg) versus f ($min^{-1}$) (constant $V_T$) resulted in a significant inverse relationship (slope=–0.062; Y-intercept=1.22; $R^2$=0.91). Thus, $P_{CO_2}$ oscillations increased in magnitude as $V_T$ increased and f decreased.

The ratio of bypass flow to total flow was similar (1:9) for the 3 mixing chamber volumes (Table 1). The time constant ($\tau$) of the bymixer response to a change in input gas concentration (at 8 L/min) ranged from 6.4 to 14.1 sec for the smallest (100 ml) to largest (200 ml) mixing chamber volumes. Tripling of the time constant predicts 95% response. During minute ventilation of the metabolic lung simulator at 4, 8, and 12 L/min, the times for 95% response of the bymixer (100 ml volume) were 19.0, 12.6, and 6.6 sec, respectively, significantly less than the values of $3\tau$ (Table 1).

Discussion

The bymixer 12 of the present invention incorporates a new design, compared to the classic bymixer. Instead of diverting a portion of main flow into a surrounding reservoir in the classic bymixer (e.g, the prior art bymixer shown in FIG. 1), the bymixer 12 of the present invention diverts a fraction of main flow through a parallel, longitudinal and adjustable mixing chamber 46. The flow resistor 50 (variable orifice) provided an easy control of fraction of bypass flow. To provide an accurate mixed average gas fraction of total flow, the ratio of bypass flow/total flow must remain constant and gas must adequately mix by the time it reaches the sampling port 48. FIGS. 3A, 3B and 3C demonstrate the excellent correlation of bymixer $P\overline{E}_{CO_2}$ compared to the simultaneous value measured in the expired gas collection, over a wide range of $V_T$, f, and $P_{CO_2}$. The Bland-Altman Limits of Agreement analysis shown in FIGS. 4A and 4B demonstrates excellent bymixer measurement accuracy, where 95% of the bymixer measurements were within 3% of the simultaneous value measured in the mixed expired gas collection. If present, the small bymixer $P_{CO_2}$ oscillations (FIG. 5 and Table 1) were time-averaged and did not degrade bymixer performance for mixing chamber volumes of 100, 150, and 200 ml.

For these mixing chamber volumes, the ratio of bypass flow to total flow was similar (1:9) because the major impedance to gas flow was the flow resistor. Increased length of the large bore tubing that formed the mixing chamber 46 tubing did not materially add to bypass flow resistance. Thus, dynamic response of the bymixer 12 can be improved by decreasing the volume of the mixing chamber 46 (e.g, in this example, by decreasing the length of the tubing). The data shown in Table 1 suggests that bymixer dynamic response (at 8 L/min) could be improved, beyond (less than) the 9.3 sec time constant of the bymixer with 100 ml mixing chamber, by further decreasing the volume of the mixing chamber 46. However, at some point, time-averaging of increasing $F_{CO_2}$ oscillations would significantly depart from the flow-averaged value and degrade bymixer accuracy. Interestingly, compared with constant gas flows (Table 1), the bymixer 12 demonstrated much faster response during mechanical ventilation of the metabolic lung simulator, presumably because the periodic, peak expiratory flows enhanced gas mixing in the bymixer 12.

There was no difference in bymixer accuracy between continuous and intermittent aspiration at the sampling port. Accordingly, the down-stream volume (measured from the sampling port) of the bypass channel was sufficiently large so that side-stream sampling (200 ml/min) did not spuriously sample gas from the main flow outlet during inspiration (when gas flow through the bymixer was zero).

The small bymixer $F_{CO_2}$ oscillations, when present, represented slight incomplete mixing in bypass flow. $F_{CO_2}$ oscillations decreased with smaller $V_T$ because the ratio of $V_T$-to-mixing chamber volume decreased. $F_{CO_2}$ oscillations decreased with higher f (at constant $V_T$) because increased overall gas flow (and velocity) improved gas mixing. The corrugations of the mixing chamber tubing presumably added to gas mixing. The presence of bymixer $P_{CO_2}$ oscillations was not significant, since simple time-averaging of the oscillations resulted in excellent bymixer accuracy (FIGS. 3A-C and 4A-B).

In summary, the novel, parallel design of the bymixer 12 provides accurate measurement of mixed expired gas fractions in the anesthesia circle circuit. Simple changes in mixing chamber volume allow adjustable bymixer response time. The fast bymixer response (time constant=6.4 sec) should permit measurements to be updated every 20 sec (where 95% response occurs by 3 time constants). The bymixer 12 of the present invention can be constructed from standard anesthesia circuit components, attaches easily to the anesthesia machine inspired outlet and expired inlet ports, is simple to clean and sterilize, and has no reservoir that can trap condensed water vapor from expired gas. This new bymixer 12 may facilitate more widespread use of indirect calorimetry ($\dot{V}_{O_2}$ and $\dot{V}_{CO_2}$) during anesthesia and the non-invasive detection of metabolic upset (e.g. onset of anaerobic metabolism) and critical events (e.g. onset of pulmonary embolism).

TABLE 1

Effect of mixing chamber volume(V) on selected parameters of the new clinical bymixer (see FIG. 2).

| Mixing Chamber V (ml) | $\tau$ (4 L/min) (sec) | $\tau$ (8 L/min) (sec) | $\tau$ (12 L/min) (sec) | Bypass Flow Ratio | $F_{CO_2}$ Oscillations (mmHg) | slope | Y-intercept | $R^2$ |
|---|---|---|---|---|---|---|---|---|
| 100 | 14.1 | 6.4 | 4.0 | 1:8.6 | 0.68 ± 0.89 | 0.995 | 0.04 | 0.9984 |
| 150 | 24.7 | 9.0 | 6.3 | 1:9.1 | 0.57 ± 0.66 | 1.001 | 0.05 | 0.9997 |
| 200 | 32.3 | 14.1 | 9.1 | 1:9.7 | 0.14 ± 0.28 | 1.010 | –0.12 | 0.9983 |

τ was the time constant of the bymixer response to a change in input oxygen concentration, measured during three constant flow rates of $O_2$. Bypass flow ratio=bypass flow/total flow. $F_{CO_2}$ oscillations were measured during continuous aspiration from the bymixer sampling port. Slope, Y-intercept, and $R^2$ (coefficient of determination) characterized the correlation of bymixer mixed expired $F_{CO_2}$ ($FE_{CO_2}$) and the value measured in a simultaneous collection of expired gas (FIGS. 3A-3C), during ventilation of the $CO_2$-producing lung simulator.

The foregoing detailed description and examples of various embodiments set forth hereabove shall not be construed in a limiting sense. The detailed description and examples are provided for purposes of illustration and description. It should be understood that all aspects of the invention are not limited to the specific depictions, configurations or relative proportions set forth herein which depend upon a variety of conditions and variables. The specification is not intended to be exhaustive or to limit the invention to the precise forms disclosed herein. Various modifications and insubstantial changes in form and detail of the particular embodiments of the disclosed invention, as well as other variations of the invention, will be apparent to a person skilled in the art upon reference to the present disclosure. It is therefore contemplated that the appended claims shall cover any such modifications, or variations of the described embodiments as falling within the true spirit and scope of the invention.

What is claimed is:

1. A bymixer device comprising:
   an inflow port connectable to a conduit such that all respiratory gas flowing through that conduit will enter the inflow port;
   a flow divider which divides the flow of respiratory gas that enters the inflow port into first and second streams;
   a main flow channel through which the first stream flows;
   a bypass flow channel through which the second stream flows;
   said bypass flow channel comprising a) a flow restrictor that restricts the flow of gas through the bypass flow channel, b) a mixing chamber positioned upstream of the flow restrictor, said mixing chamber comprising tubing that is alternately extendable and contractible so as to enable a user to alternately increase and decrease the volume of the mixing chamber; and c) sampling apparatus for sampling respiratory gas from said mixing chamber;
   a flow combiner that combines the first and second streams after they have passed through the main flow channel and bypass flow channel to form a combined outflow stream; and
   an outflow port that is connectable to a conduit such that the combined outflow stream enters that conduit.

2. A bymixer device according to claim 1 wherein the flow restrictor is variable.

3. A bymixer device according to claim 1 wherein the main flow channel comprises a substantially rigid plastic tube.

4. A bymixer device according to claim 3 wherein the sampling apparatus is selected from the group consisting of:
   a port through which a sample of gas may be removed from the mixing chamber; and
   a sensor positioned so as to sample gas within the mixing chamber.

5. A system comprising a bymixer device according to claim 1 further in combination with a monitoring device that is connected to the sampling apparatus and useable to determine at least one variable in gas sampled from the mixing chamber.

6. A system according to claim 5 wherein the monitoring device comprises a device useable for performing capnography or calorimetry.

7. A system according to claim 5 wherein the monitoring device is operative to determine and/or compute at least one variable selected from the group consisting of:
   average alveolar $PCO_2$
   volume-averaged alveolar $PCO_2$ ($\overline{PE}_{CO_2}$);
   $CO_2$ elimination ($\dot{V}_{CO_2}$);
   pulmonary oxygen uptake ($\dot{V}_{O_2}$);
   concentration or partial pressure of volatile gases; and
   concentration or partial pressure of non-volatile gasses.

8. A system according to claim 5 further comprising a display apparatus connected to or formed integrally of the monitoring device for displaying at least one variable determined by the monitoring device.

9. A system according to claim 5 further comprising computing apparatus for computing one or more calculated values using at least one variable determined by the monitoring device.

10. A system according to claim 9 wherein the computing apparatus is programmable.

11. A system according to claim 9 wherein the computing apparatus comprises a microprocessor.

12. A system according to claim 9 wherein the system receives data required for and is equipped to calculations one or more values selected from the group consisting of:
   Minute Ventilation ($\dot{V}_E$);
   Tidal Volume ($V_T$);
   Inspiratory Reserve Volume (IRV);
   Expiratory Reserve Volume (ERV);
   Total Lung Capacity (TLC);
   Functional Residual Capacity (FRC);
   Vital Capacity (VC);
   Pulmonary Oxygen Uptake Per Breath ($V_{O_2,br}$); and
   Pulmonary Carbon Dioxide Elimination Per Breath ($V_{CO_2,br}$).

13. A ventilation circuit for use in ventilating a human or veterinary patient, said ventilation circuit comprising:
   a) an inspiratory flow conduit that carries a flow of inspiratory respiratory gas for delivery into the patient's lungs;
   b) an expiratory flow conduit for carrying expired respiratory gas that has been expelled from the patient's lungs;
   c) a first bymixer device connected to the inspiratory flow conduit such that samples of mixed inspiratory respiratory gas may be obtained from a sample port of the bymixer; and
   d) a second bymixer device connected to the expiratory flow conduit such that samples of mixed expiratory respiratory gas may be obtained from a sample port of the bymixer;
   wherein each of said first and second bymixer devices comprises; i) a flow divider for dividing the flow of respiratory gas into first and second streams; ii) a main flow channel through which the first stream flows; iii) a bypass flow channel through which the second stream flows, said bypass flow channel comprising a flow restrictor that restricts the flow of gas through the bypass flow channel, a mixing chamber positioned upstream of the flow restrictor and sampling apparatus for sampling respiratory gas from said mixing chamber.

14. A ventilation circuit according to claim 13 wherein the ventilation circuit is an open circuit wherein expired respiratory gas is not recycled into the inspiratory flow conduit.

15. A ventilation circuit according to claim 13 wherein the ventilation circuit is a closed or circle circuit wherein expired respiratory gas is recycled into the inspiratory flow conduit.

16. A ventilation circuit according to claim 15 further comprising a carbon dioxide absorber for removing at least some carbon dioxide from the expired respiratory gas before it is recycled into the inspiratory flow conduit.

17. A ventilation circuit according to claim 15, further comprising a fresh gas inflow conduit for combining fresh respiratory gas with recycled expired respiratory gas such that the inspiratory flow conduit carries a mixture of fresh respiratory gas and recycled expired respiratory gas.

18. A ventilation circuit according to claim 13 wherein the bymixer is connected to the inspiratory flow conduit such that samples of mixed inspiratory respiratory gas may be obtained from the sample port of the bymixer.

19. A ventilation circuit according to claim 13 wherein the bymixer is connected to the expiratory flow conduit such that samples of mixed expiratory respiratory gas may be obtained from the sample port of the bymixer.

20. A ventilation circuit according to claim 13 further comprising a source of anesthetic gas such that inspiratory respiratory gas that flows through the inspiratory flow conduit includes at least one anesthetic gas.

21. A method for sampling mixed respiratory gas in a ventilation circuit for ventilating the lungs of a human or veterinary patient, said ventilation circuit including at least one inspiratory flow conduit through which inspiratory respiratory gas flows for delivery to the patient's lungs and at least one expiratory flow conduit through which expired respiratory gas flows after having been expelled from the patient's lungs, said method comprising the steps of:
A) providing a bymixer device which comprises i) an inflow port connectable to a conduit such that all respiratory gas flowing through that conduit will enter the inflow port; ii) a flow divider which divides the flow of respiratory gas that enters the inflow port into first and second streams; iii) a main flow channel through which the first stream flows; iv) a bypass flow channel through which the second stream flows, said bypass flow channel comprising a flow restrictor that restricts the flow of gas through the bypass flow channel, v) a mixing chamber upstream of the flow restrictor, said mixing chamber comprising tubing that is alternately extendable and contractible to enable a used to alternately increase and decrease the volume of the mixing chamber; vi) sampling apparatus for sampling respiratory gas from said mixing chamber; vii) a flow combiner that combines the first and second streams after they have passed through the main flow channel and bypass flow channel to form a combined outflow stream; and viii) an outflow port that is connectable to a conduit such that the combined outflow stream enters that conduit;
B) connecting the inflow port of the bimixer to a first respiratory gas flow conduit and the outflow port to a second respiratory gas flow conduit such that respiratory gas flows through the bypass channel and becomes mixed in the mixing chamber; and
C) using the sampling apparatus to sample mixed respiratory gas from mixing chamber.

22. A method according to claim 21 wherein Step C comprises withdrawing a sample from the mixing chamber.

23. A method according to claim 21 wherein Step C comprises positioning a sensor within the mixing chamber and measuring a component of the gas within the mixing chamber by way of said sensor.

24. A method according to claim 21 further comprising the step of:
D) determining at least one variable from mixed respiratory gas sampled in Step C.

25. A method according to claim 24 wherein Step D comprises performing capnography on mixed respiratory gas sampled in Step C.

26. A method according to claim 24 wherein Step D comprises performing calorimetry on mixed respiratory gas sampled in Step C.

27. A method according to claim 24 wherein Step D comprises determining and/or computing at least one variable selected from the group consisting of:
volume-averaged alveolar $PCO_2$ ($\overline{PE}_{CO_2}$);
pulmonary carbon dioxide elimination ($\dot{V}_{CO_2}$);
pulmonary oxygen uptake ($\dot{V}_{O_2}$);
concentration or partial pressure of volatile gases; and
concentration or partial pressure of non-volatile gasses.

28. A method according to claim 21 further comprising the step of determining one or more values selected from the group consisting of:
minute ventilation ($\dot{V}_E$);
tidal volume ($V_T$);
Total Lung Capacity (TLC);
Functional Residual Capacity (FRC);
Vital Capacity (VC);
pulmonary carbon dioxide elimination per breath ($\dot{V}_{CO_2, br}$); and
Pulmonary Carbon Dioxide Elimination Per Breath ($V_{CO_2, br}$).

29. A method according to claim 21 wherein the method further comprises the step of:
D) changing the size of the mixing chamber.

30. A method according to claim 21 wherein the degree of flow restriction caused by the flow restrictor is variable and wherein the method further comprises the step of:
D) varying the degree of flow restriction caused by the flow restrictor to change the flow rate of gas through the mixing chamber.

31. A method according to claim 21 wherein the first and second respiratory gas flow conduits comprise first and second portions of an inspiratory gas flow conduit.

32. A method according to claim 21 wherein the first and second respiratory gas flow conduits comprise first and second portions of an expiratory gas flow conduit.

* * * * *